United States Patent [19]

McCarthy

[11] Patent Number: 5,161,545
[45] Date of Patent: Nov. 10, 1992

[54] UNIVERSAL LIMB RESTRAINT DEVICE

[76] Inventor: Andrew D. McCarthy, 5507 Albia Rd., Bethesda, Md. 20816

[21] Appl. No.: 723,049

[22] Filed: Jun. 28, 1991

[51] Int. Cl.[5] .............................................. A61F 5/37
[52] U.S. Cl. .................................... 128/878; 128/876
[58] Field of Search ............... 128/846, 869, 874, 876, 128/878, 879, 881, 882

[56] References Cited

U.S. PATENT DOCUMENTS

| 2,606,554 | 8/1952 | Simon | 128/881 |
| 2,706,477 | 4/1955 | Daake | 128/878 X |
| 3,027,895 | 4/1962 | Williams | 128/878 |
| 4,414,969 | 11/1983 | Heyman | 128/878 |
| 4,628,925 | 12/1986 | Witzel | 128/878 |
| 5,016,650 | 5/1991 | Marlar | 128/878 |

Primary Examiner—Robert A. Hafer
Assistant Examiner—Brian E. Hanlon
Attorney, Agent, or Firm—Arthur R. Eglington

[57] ABSTRACT

A limb restraint device adapted to limit excess limb flexing including a padded, flexible fabric member of a rectangular configuration, an attached flexible cloth means consisting of a closed circle mounted thereon to form two symmetrical loops adapted for double looping about the operating padded member, a final pair of complemental pile and look-locking segments mounted at one longitudinal end of a first planar surface of the padded fabric member and a second pair of such segments mounted at the other longitudinal end of the padded member and located on the opposing planar surface thereof.

A separable anchoring strap engages slidably with the symmetrical loops of the padded cloth means, also being provided with opposing and mateable elements which form an anchor strap joinder and release means. The cooperating padded cuff and anchoring strap provide for the overall flexing play of the thusly restrained limb.

3 Claims, 3 Drawing Sheets

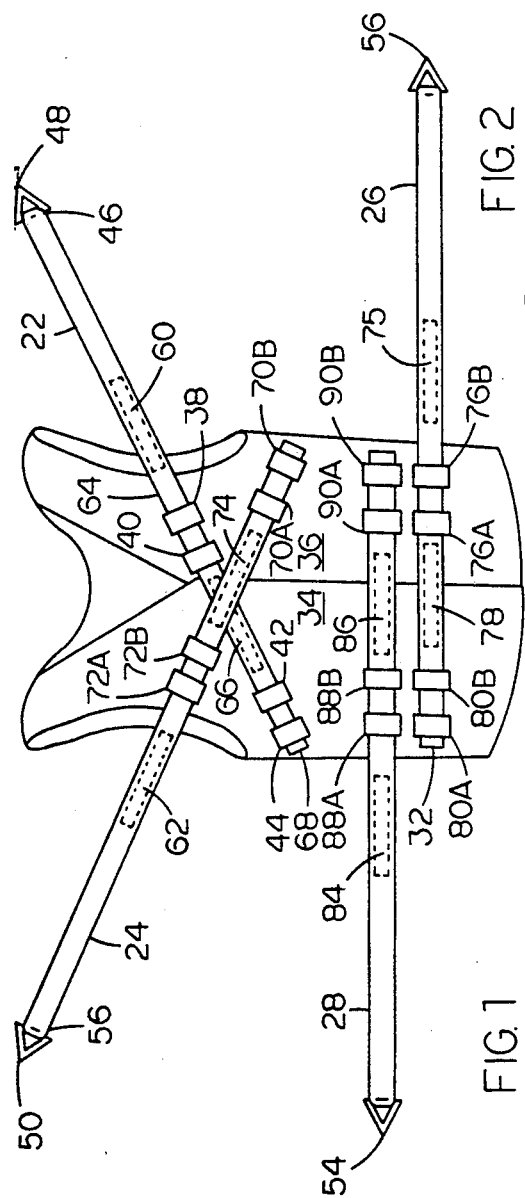
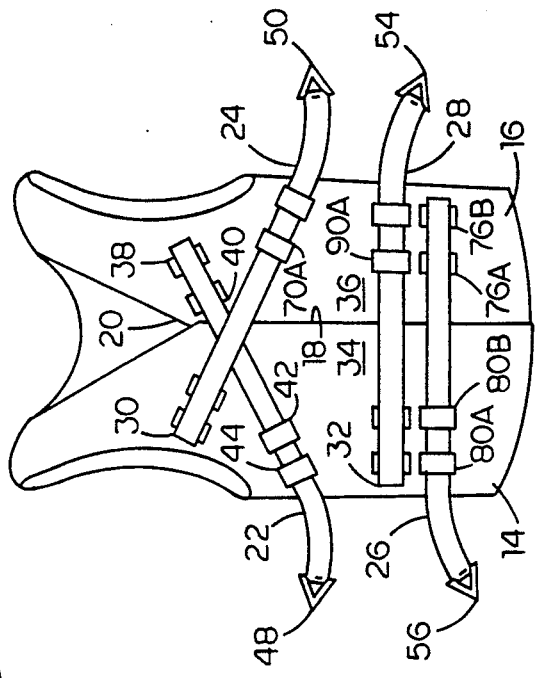
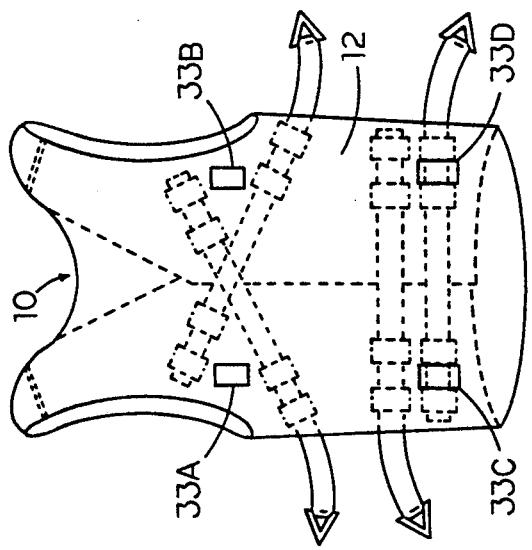

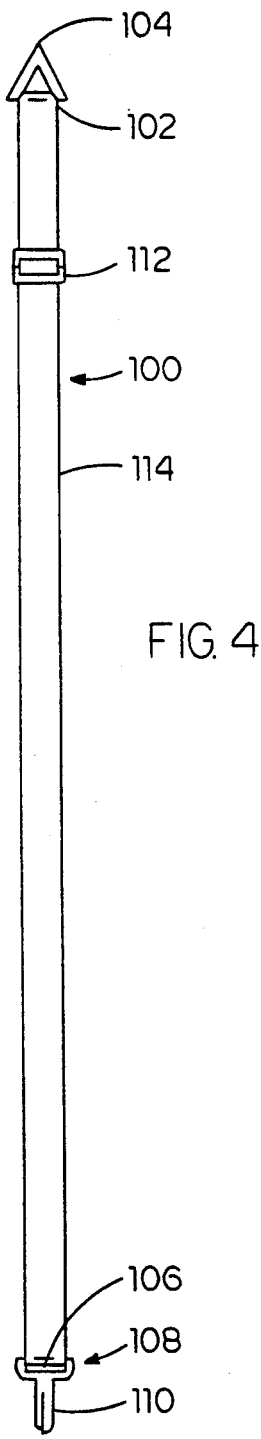
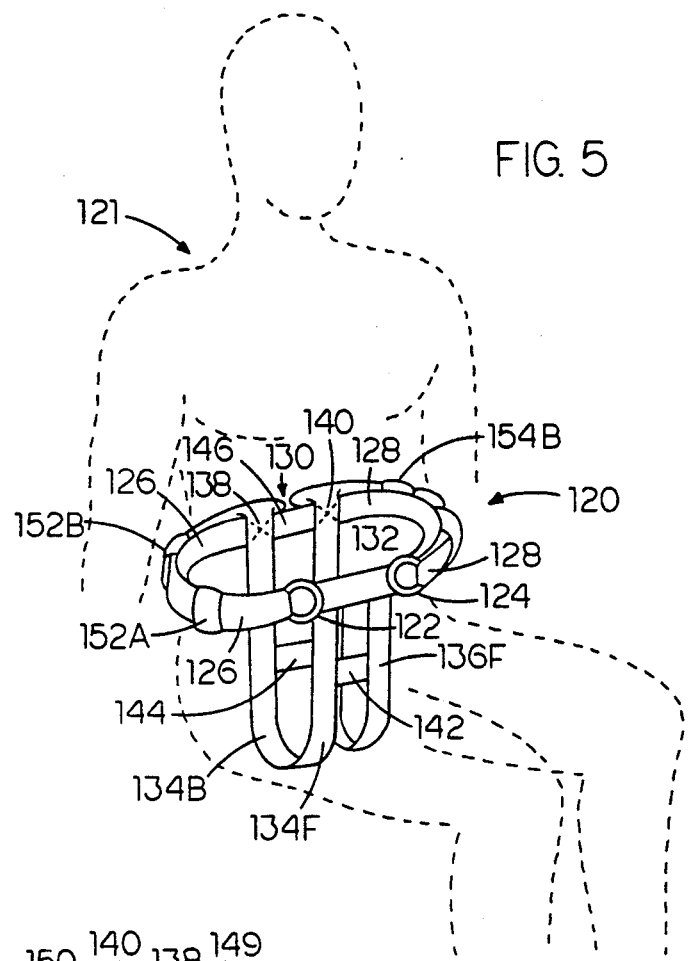
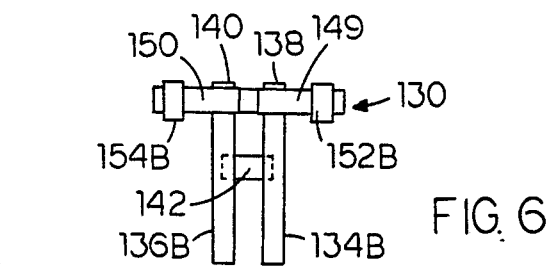
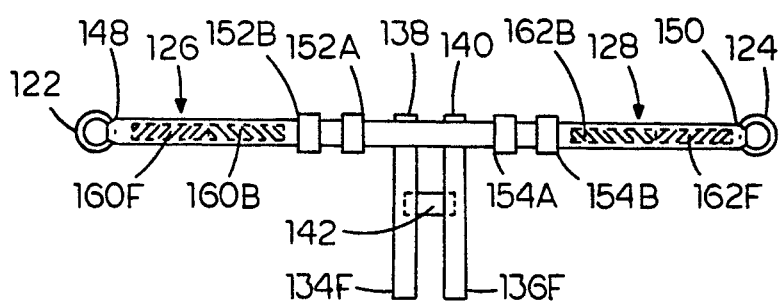

UNIVERSAL LIMB RESTRAINT DEVICE

TECHNICAL FIELD OF THE INVENTION

This invention relates to a new device for restraining patients against unsafe (and spontaneous) movement by securing them to supports or fixtures. In one of its more specific aspects, the invention is concerned with a specially configured patient restraint device with multiple means for safely securing, and releasing, a patient to various supports.

The present invention also discloses safety belts for a chair-bound patient to preclude slipping down and out of the chair. The unique belt is cooperatively associated with the safety vest proper.

BACKGROUND OF THE INVENTION

A wide range of patients must be protected against unsafe and unhealthful movement—principally falling out of body supports such as a bed, tables and chairs, or by moving their body portions, and thereby rupturing sutures, or otherwise causing further injury to already impaired body portions. Without being secured in such supports by health care personnel, such patients are likely to cause serious injury to themselves. Such patients include comparative invalids, as well as those who have sufficient consciousness and strength to attempt to disengage such restraints; or to engage in substantial movement, but who are also subject to sufficient aggression, disorientation, or other debilitating condition, that disengaging their own restraints would likely result in injury to them. However, since the subject being restrained is a patient who is suffering from a medical disability, such restraint must be comfortable and not overly confining in use to be acceptable.

Manually tied restraint devices are shown in the vests of U.S. Pat. Nos. 4,488,544 and 3,265,065, among others.

U.S. Pat. No. 3,136,581 is directed to an infant's Harness, comprising a vest A of a back panel 10, front panels 12, 14 one strap 16 and a ring 18. It lacks paired fastening straps and companion anchoring straps adapted for interlinking loop means. The sole fastening strap 16 and 20 simply wrap around a chair back 28. U.S. Pat. No. 4,117,840 to Rasure is directed to a Pediatric restraint garment, basically for a bed-ridden child patient to inhibit torso movement, both longitudinally and transversely. It has a flap-like extension 22 from central panel member 18 to overlap front panel 16. A plurality of parallel, contact-fastening strips 24 form the vest closure. Such Velcro-type fasteners are located so as to be readily undone by an adult patient.

The act of strap tying is itself somewhat awkward and time-consuming for valuable health care personnel, particularly with an agitated patient.

Prior art tie-less restraint devices are bulky, complicated, restrictive in use, or they provide securing means which are accessible to the patient, and thus are susceptible to patient disengagement. Additionally, such devices pose special risks to patient safety.

Long-used restraint devices, are medically recognized as capable of serious mishap. Certain devices are described as dangerous; yet necessary evils in geriatric medicine; *Journal of Kentucky Medical Association*, August 1986, p. 397 et seq.; "Accidental Deaths in Aged Using Protective Devices." Recent reports in the *Journal of the American Medical Association* (JAMA), report several deaths caused by these vests in nursing homes, including cases of strangulation due to vest restraints and proposals that current vests be used more judiciously; JAMA, Nov. 21, 1986—Vol. 256, No. 19, p. 2724; and JAMA, Nov. 21, 1986—Vol. 255, No. 7, p. 905.

In sum, despite their long history of use and the variety of forms offered, serious mishaps do occur to agitated patients, even when currently available vest restraints are employed.

A newer form of a universal, tie-less patient torso restraint device is disclosed and claimed in my U.S. Pat. No. 4,832,053, issued May 23, 1989. It embodies several components also seen in the presently described torso restraint vest. However, the presently disclosed vest presents a number of practical features not specifically taught or suggested by the '053 patent. My earlier restraint, while already enjoying professional acceptance, does not lend itself as well to the situations in which the vest required size adjustments to fit different torso configurations, and also did not allow enough chest movement for free & easy respiration.

It is an object of the present invention to provide an improved torso restraint which is not subject to the above described limitations and hazards in use; and which is simple to secure and facile to release by the attending personnel. It is a further object of the invention to provide a garment which is readily formable into a vest and is tethered by a plurality of straps that are consistently secured and quickly releasable by the therapist.

It is a further object of the invention to provide a restraint vest wherein the tethering straps are individually adjustable to enable minimal patient shifting while restrained and thus preclude mattress sores. It is a further object of the invention to provide a restraining vest from which the patient can be removed more handily than is possible with currently used restraints, sometimes entailing separately tied knots for the strap anchoring.

A still further object of the invention is to provide a belt-like harness for the lower patient torso, which cooperates with the present vest restraint and so precludes a vested patient, who is also a chair-bound, from wriggling down and out of the supporting chair even while his upper torso is adequately vested.

Other objects and advantages of the present invention will become apparent from the following specification and from the drawings and the claims.

BRIEF SUMMARY OF THE INVENTION

In accordance with the invention, a vest-like patient restraint is provided which comprises a unitary vest garment, preferably composed of a flexible material, and with neck and arm apertures, including a unitary front panel, and a pair of spaced-apart back panels with opposing edges, as shown in the accompanying drawings, and a pelvic safety belt cooperatively associate with the vest, in which:

BRIEF DESCRIPTION OF THE DRAWING

FIG. 1 is an elevational front panel view (chest-side) of the vest restraint of the present invention;

FIG. 2 is an elevational view of the reverse panel of the vest garment of FIG. 1, showing the adjacent vest panels and the dual pairs of their cooperating fastener straps, as when secured about a patient and ready for terminal anchoring;

FIG. 3 is another plan view of the vest reverse panel but with the drawing back of the free ends of the fastener straps to depict the underlying fastener segments and their adjacent complimentary segments on the extended fastener straps;

FIG. 4 is a plan view of the anchoring strap component of the invention, functionally identical to the anchoring strap depicted in FIG. 4 of my U.S. Pat. No. 4,832,053, but modified slightly as to one of the terminal mating elements at its longitudinal end, with such anchoring strap being securable to remote stationary posts in a ready manner, (as FIGS. 5, 6, and 7, next to be described);

FIG. 5 is a perspective view of the chest side of a safety belt adapted for a patient's lower torso useful in cooperation with the safety vest described in FIGS. 1 to 3, and showing a restrained (partial) patient torso in phantom;

FIG. 6 is an elevational view of the reverse side of the safety belt of FIG. 5, as it protectively engages a seated patient's lower rear torso, and also depicts an offset pair of spaced-apart, vertical harnesses which embrace the patient's buttocks;

FIG. 7 is an elevational view of the safety belt device (stomach side) but with the extending out of the unfastened free ends so to depict the underlying complemental set of fastener segments located on each of the respective extended fastener straps, which engage securely during the looping back, leaving the ring-like, other ends adapted for anchor strap coupling;

DETAILED DESCRIPTION OF THE PREFERRED EMBODIMENT

Figure 8:
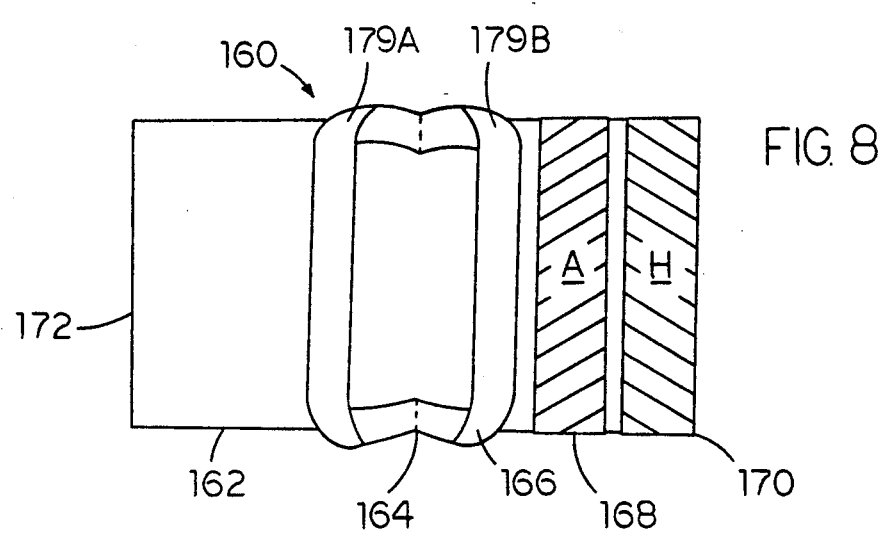
FIG. 8 is an elevational view of one surface of a device used for patient wrist restraint, depicting a centrally mounted loop-like fastening means and one of the end sets of adjacent, complemental fastener pads.

Each of the back panels has preferably at least two, spaced-apart vest-fastening straps extending towards the opposing back panel with each such strap extending through an integral loop means and terminating at its free end in a rigid ring-like attaching means. Thus, there are four vest-securing (fastening) straps, in all, and a like number of anchoring ends.

Also provided to cooperate with each of the fastening straps, is a discrete, elongated anchoring strap, the body of which loops through a ring attaching means provided on the free end of the vest fastening straps. A vest with four fastening (securing) straps in use will require four anchoring straps. Each anchoring strap is of a variable length, but is always sufficient for it to also be looped around, preferably with a double-pass, the periphery of a stationary support post, which is conveniently a horizontal bar or railing on the bed itself, or it can be a distal stanchion pipe (See FIGS. 5 and 6 of my U.S. Pat. No. 4,832,053). The free ends of the anchoring strap terminate in mateable elements which form a single end attachment and release means, that closes the loop of the strap, while it is secured simultaneously to the fastener strap ring and the stationary post.

As shown in the drawings, and in FIG. 1 in particular, the restraint vest, generally 10, of the present invention is fabricated of any suitable flexible material, such as a strong cloth, either of woven textile or vinyl coated fabric. It comprises an integral wrap-around-the-torso vest, having an integral front panel 12, which enfolds rearwardly to form a pair of opposing left and right panels 14 and 16 (FIG. 2), having then respective substantially vertical edges 18 and 20.

In use, such vertically-oriented edges are spaced apart a varying distance, dependent upon the girth of the particular patient. The vest may be fabricated in several sizes. Each of the reverse (back-side) panels 14 and 16, and proximal to their vertical edges 18 and 20, have secured thereto two pairs of spaced-apart, fastening straps 22, 24, 26, and 28 (four in all). Each of upper opposing strap pair (22, 24) are secured at the one end, like 30, to have a conveniently, upwardly-inclined orientation, when extended; meanwhile lower straps 26 and 28 are secured at their inner ends, like 32, to project in a generally horizontally orientation, when extended. Such straps may be usefully oriented in other juxtapositions.

Secured in squared configuration upon the front panel 12 of vest 10 are four, comparatively larger, flexible loops, 33A/D, arrayed in a horizontal upper pair (33A/B) and horizontal lower pair (33C/D). These particular loops are to be coupled with discrete anchoring straps (FIG. 4), so as to secure a patient in a prone sideways position (the upper loops being engaged;) or alternatively, for a seated patient, for the coupling along the vest 10 lower margin of the pelvic safety belt, described in relation to present FIGS. 5 to 7.

At the one tied end, the fastening straps are each separately attached to the overlappable vest vertical margins 34 and 36 of the back panel portions, as by edge-sewing, or the like. In the illustrated embodiment (reverse panel) of FIG. 2, each fastening strap extends laterally from and across its respective supporting margin towards, and to at least substantially overlap, the opposing back panel (e.g., upper strap 22 over panel 34), also normally passing through a suitably-aligned paired flexible loops 38-44, all composed of a reinforced fabric, or the like. Dual sets of closely-spaced, panel mounted loops are preferred for engaging each fastening strap, like 22.

For example, upper strap 22, originating at, and secured to, near the lateral upper margin of panel 34, extends and inclines across any vertical gap between the abutting panel edges (not shown), over to adjacent panel 34, then through loops 42 and 44, leaving its free end 46 available for a lateral attachment, to be described.

The free ends of each of the four fastener straps, 22-28, terminate in a preferably rigid, closure means, 48-54, such as a triangular ring, either of metal or plastic. Each clasping ring is retained in place by doubling back the strap fabric free end, enclosing same over the ring base portion, and conventionally securing, as by seam sewing, or the like.

The vest-mounted fastener straps are all of a preselected finite length, so that even with a torso of comparatively large girth, they are of a length sufficient, such that the ring end, like 48 on strap 22, will at least extend through the opposing loop pair 42, 44, and extend beyond them at least several inches or more, so as to permit ring coupling to another strap component of the invention, to be described (FIG. 4).

In FIG. 3 is depicted another elevational view of the reverse side of the restraint, but with the four fastener straps being projected outwardly for clarity in seeing the improved supplemental strap securing means and cooperating strap guide loops of the present invention.

An uppermost pair of adhering pads 60/62 are affixed proximal to the free ends 30/56 of inclined anchoring straps 22 and 24, respectively; for strap 22, while the intermediate segment 64 of strap 22 passes through soft loops 38,40, before presenting a second pad 66 (of the hook-locking type) which is affixed proximal to the tie end 68 of such inclined strap 22. A second pair of soft loops 42,44 are located adjacent to the tied end 68. Similarly so with opposing upper inclined strap 24, which presents inner paired loops 70A, 70B, outer paired loops 72A, 72B, inner adhering pad 74 and outer hook-locking pad 62, terminating in ring closure means 50.

A similar arrangement of double-paired loops and complementary dual, Velcro-type holding means are provided on each of the lower horizontal anchoring straps 26 and 28. For example, horizontal strap 26 has outer hook-locking pad 75, outer double loops 76A, 76B, inner adhering pad 78, and inner double loops 80A/B, terminating at inner strap end 32.

Opposing strap 28 has its Velcro pad pair 84 and 86, spaced-apart, dual sets of loops 88A/B and 90A/B, all to be used as will be detailed. Broadly, the outer pads cooperate adheringly with the complimentary pad segments on the inner straps, are reinforced by passing through the inner and outer looped pairs, before emerging for free-end coupling, as seen in FIG. 1.

Such securing feature for the strap body, serves to provide a safe and comfortable fit for the restraint, which is independent of the movement-limiting functioning of the cooperating anchoring strap of FIG. 4, like 100. Such Velcro-type ancillary fastening means on the vest back panels will also reduce the risks already seen with loosely fitting restraint vests, and from too-loose vests slipping into a ligature mode, and possibly obstructing patient ventilation, as has been reported in the medical literature, as discussed earlier.

Conveniently, the opposing upper pads, like 60 and 66, are of the well known Velcro adhesive pile and complementary hook-locking means, such are manually compressed after the straps are in place. The adhered pads can be handily separated when the vest is to be removed, by manually pulling apart the Velcro locking pad means, and by retracting the fastener strap end rings, like 48 to the FIG. 3 position, back through loop pairs 42/44 respectively. The restraint 10 is quickly removed from the patient, as needed.

In FIG. 1, as noted, there is shown how the restraint vest of the present invention appears from the chest-side, (while being worn by the patient—not seen), but now ready to be coupled with next-to-be-described elongate anchoring straps. Each fastening strap end, like 48, extends radially from the hidden portion of the safety vest to cooperate with such discrete anchoring straps, which may also connect to stationary posts (see FIGS. 5 and 6 of U.S. Pat. No. 4,832,053).

In. FIG. 4, is a top plan view of the anchoring strap component 100, laid out in its full extension, as it would appear before its use in the present invention. At its one longitudinal end 102, the anchor strap terminates in a rigid, triangular attachment means such as a metal (or formed plastic) ring 104. This ring can be secured similarly to rings 52, 54, employed on the free ends of the fastener straps 26, 28.

The other longitudinal end of anchor strap 100 is looped through a transversely configured, rigid slot 106 of fastener 108. Slot 106 is integral with the conventional spring snap fastener 108, typically one with a partial hook-shaped rigid end and a cooperating flexible metal (or plastic) snap strip 110. Strip 110 is biased to be normally closed within the inner tip (not seen) of the hooked end. Strip 110 is adapted to be manually depressed so as to permit instant release of any ensnared ring, like closure means 52 (FIG. 1).

Ring means 104 of anchor strap 100 (FIG. 4) is the one with which the other complemental snappable joinder means 108 will cooperate, after the anchoring strap 100 is properly looped through a vest fastener strap rings, like 52. The elongate free fabric portion of anchor strap 100, which is located intermediate ring 104 and snap fastener 110 (not seen), is held by a conventional double-slot, rigid buckle 112. The slidable buckle 112 tracks itself along on the free fabric length 114 of the anchor strap 100 proper. In this manner, the overall length of anchor strap 100 is substantially variable, but is still presetable, so as to tightly straddle the distance between the vest attachment point (fastener rings 52/54), and the particular type of remote stationary post(s), to be employed with the vest while in use.

It is important (for non-accessibility to the restrained patient), where the anchoring strap is positioned, and where its ends are joined relative to the cooperating fastening strap loop, and to an anchor point, like a railing 39 (FIG. 5 of U.S. Pat. No. 4,832,053).

In the step of coupling with, and limiting the movement of, the fastening straps, like 22, the rigid ring 104 of the anchor strap is first positioned adjacent the exterior surface of the horizontal length of the railing 39, as best shown in above-identified FIG. 5, of U.S. Pat. No. 4,832,053. Then, the clip fastener end 106 of the strap 100 is slipped through partly exposed loop 104, and both are cinched tight against bed railing. Then, free end 102 is extended upwardly to pass through end ring 52 of the fastener strap 26. The free end 102 is doubled backward toward the railing 39, so as to be linkable with rigid ring 104. However, strap end 102 is first slipped under railing 39, before being snapped over rigid ring 104 (FIG. 6 of U.S. Pat. No. 4,832,053).

This manner of linking with fastening strap 52 negates any shifting of the anchor strap ring 100 during the course of erratic patient movement while he is in the restraint garment 10. The overall reach of the thusly closed anchor strap is, of course, presetable by the use of sliding buckle 112.

As for the juxtapositions of the Velcro fastener, as to its complemental components, the adhesive pile component may be more conveniently mounted proximal to the tied ends of the fastening straps, while the multiple hook pads are mounted proximal to the free ends of the fastener straps. Either arrangement is operable, but that just described is preferred for ease of manipulation of fastening straps.

An ancillary device that can be usefully employed with the just described safety vest is the belt restraint means of FIGS. 5 to 7. In the perspective view of FIG. 5, such a safety belt 120 is depicted, as it would appear mounted on the lower torso of a seated patient 121, who may also be wearing a safety vest, as well (FIG. 8). If so, the free ringed ends 122, 124 of dual horizontal belting straps 126 and 128 of belt 120 would be threaded through lower loops 33C and 33D on vest 120, before they are doubled back to engage rear midsection 130 for secure fastening, as will be described.

The front midsection 132 of belt 120 presents a spaced-apart, pair of vertically oriented restraining straps 134F and 136F, which then are passed under the patient crotch and buttocks, to circle back so as to be securely attached via terminal end loops to the backside 130 of the belt, i.e., to double-looped horizontal belt mid-segment 146.

To maintain suitable positioning athwart the lower torso, at least two connecting segments 142 and 144 span the gap between the frontal and backside runs of the parallel vertical straps 134 and 136. The rear segment 130 of belt 120, also has upper connecting segment 146, which is flanked laterally by the permanently looped ends of vertical straps 134B, 136B. Vertical rear loops 138 and 140 (also FIG. 7) are permanently secured to either end of the horizontal mid-segment 146, and serve as the doubling back terminal for the free ends 148, 150 of belt forming straps 126 and 128, as shown.

Each of the free ends of belt forming straps 126 and 128 are provided with a ring-like element 122, 124, respectively, which will engage the snap-clip ends 108 of the cooperating anchoring straps 100 (FIG. 4), which were described above. Proximal to the lateral sides of straps 126/128 mounted vertically-oriented, flexible pairs of loops 152A/B, and 154A/B, respectively, through which the belt strap free ends 148/150 are passed, before their snap-clip engagement with associated anchoring straps.

In the reverse-side view of FIG. 6, the mode of fixed rear attachment of buttocks-encircling vertical straps (134B/136B) to the double back runs of the horizontal belt loops is shown. Also, near the lateral sides of horizontal belt segment 126/128 are vertically oriented, outer soft loops 152B and 154B, which also serve to contain the closed free ends 148/150 of belt straps 126/128, when a patient of large lower girth is being protected.

The elevational view of FIG. 7 is of the safety belt front side, but depicted with the horizontal belt straps 126, 128 disengaged from their functional, Velcro-type retention. This reveals the substantial length, of the underlying pad of complementary fastening material, fixedly mounted on the horizontal belt. Preferably, the adhesive pile segment is on the inner belt portion 160/162B, and the hook-locking segment 160/162F, is disposed on the outer strap portion.

Both the restraining vest and cooperating safety belt of the present invention provide a marked improvement over earlier known garments. They provide for secure restraining means, which cannot be released by the restless patient, since the sliding buckles, like 112 and the snappable fastener, like 110 on anchoring strap 100, are located distally from a patient; yet, it is these components that are comparatively inexpensive to fabricate, requiring no unusual hardware. They also involves no integral component which can become hazardous to the patient.

In actual use with a patient, addressing the opened vest 10 from the back, one takes up the free end 46 of upper strap 22, doubles it back over paired vest loops 38/40, and thread it through loops 42/44 on opposing back panel 34, with the result as appears in FIG. 2. Similarly, take left side fastening strap 24, double it back over outer vest loops 72A/B, and thread it through inner loops 70A/B on the opposing back panel 36, with the combined result as appears in FIG. 2.

Next, follow the same strap doubling and threading procedure for lower horizontal straps 26, 28; for example, by doubling strap 26 back over loops 76A/B, threading through 80A/B, and extending ring 52 outwardly. Lastly, double strap 28 back over loop 88A/B, threading through loops 90A/B, and extend ring 54 outwardly for anchor strap coupling. Again, the result is as appears in FIG. 2.

With the safety vest properly suited to the patient torso, one is ready to anchor the so-vested patient in a variety of situations. The anchoring strap of FIG. 4 can be used to secure a vested patient to a bed (as described in my U.S. Pat. No. '053), or in a wheelchair, or in a safety chair. As noted, anchoring strap lengths are readily adjustable 112, having its ring closure 104 at one end and snap hook 108 at the other end. The strap lengths are adjustable for comfort and security of the patient.

Also, anchoring straps like 100 can remain attached to the bed frame after release of the fastening strap, and thus are ready for hook-up to the safety vest at any time.

Safety belt 120 of FIGS. 5 to 7, can be employed in conjunction with the safety vest of FIGS. 1 to 3, so as to provide added security with a seated patient. Firstly, left end ring 122 of the belt passes through one lower loop 33D on the vest front panel 12. Be sure that both front loops (152A/154A) on the belt pass through the loops on the vest. Repeat the step, threading the other belt ring 124 through the opposing front loop 33C on the vest. Again, both the belt strap free ends should slide through the vest loop. Later, when resorting to the anchoring straps, one will need to couple the belt rings 122/124, with the strap rings like 108.

The dual strand, webbed material, elongate crotch strap should be passed between the patient's legs and doubled back to the rear panels on the vest. To connect this webbed section to the side belt strap, thread each belt ring, 122/124, through one loop 138 on the terminal end of the webbed section. Double back the strap 126 free end 148, matching the Velcro pad in the strap center, and then thread the ring 122 of the belt through the dual side loops 152A/B.

Repeat these steps for the other belt strap 128, threading, doubling back and matching the Velcro pads, finally threading end ring 124 through paired loops 154A/B. Now, the integrated safety vest and belt are properly enclosed about the patient who has been secured, as needed, in a wheelchair, or safety chair. Safety belt 120 is not usually employed with a bed-ridden patient.

Most impressively, it handily permits necessary readjustments of the patient's body, without risking an injurious fall from the supporting bed, or any contortions by an agitated patient that could convert the vest edges into a strangulation ligature, as has been discussed.

Figure 9:
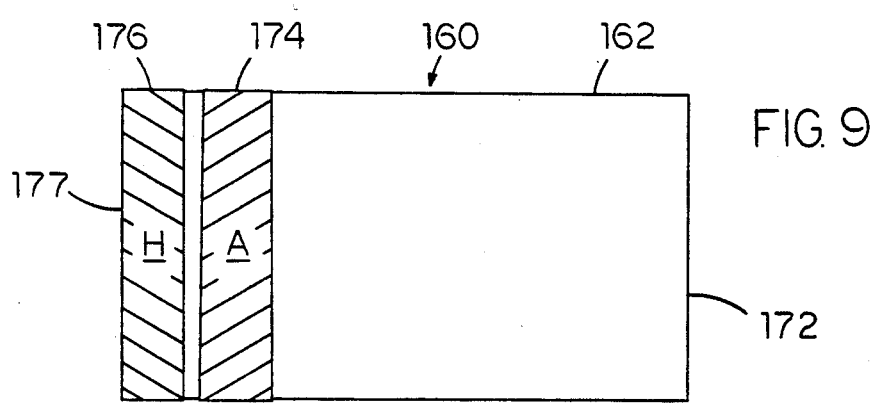
FIG. 9 is an elevational view of the opposing planar surface of the wrist restraint device of FIG. 8 depicting the other end set of complemental fastener pads, being used with the above described restraint and safety belt.
Figure 10:
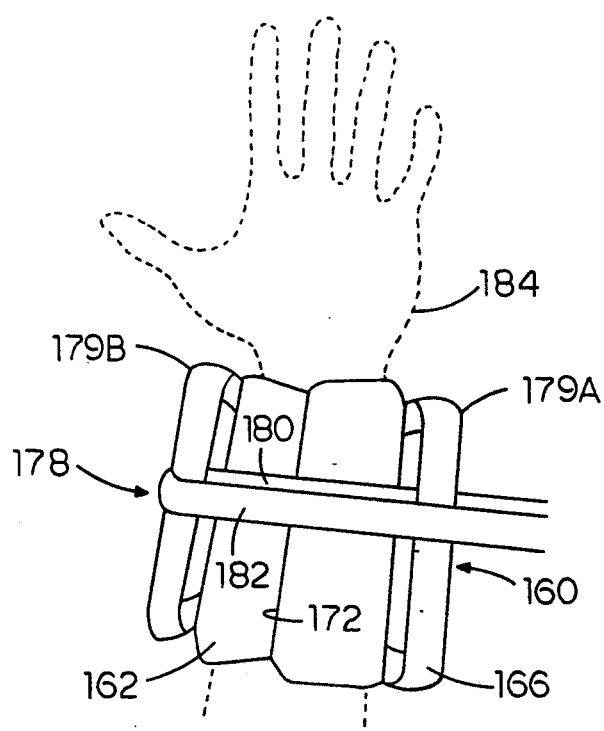
FIG. 10 is a perspective view of one of the wrist restraint devices cradling a patient forearm, and with loop-like means now operatively associated with the intermediate length of an anchoring strap of FIG. 4.

The ancillary device of a wrist-cuffing means of FIGS. 8 to 10, is provided for those agitated patients needing limb protection, as well. The cuffing means has a fully padded, flexible fabric base member, which is mateable with complimentary pairs of Velcro adhering pads and a loop-like fastening means. As will be described, the wrist-engaging cuffing means is thusly coupled to a separate anchoring strap (FIG. 4), which may be secured to the bed-frame, as seen in FIGS. 5 and 6 of my U.S. Pat. No. 4,832,053.

The wrist restraint device 160 of FIG. 8 is comprised essentially of a flexible, but strong, rectangular, integrally-padded, woven cloth 162, (such as a core composed of foam-shaped rubber) on which surface are mounted certain elements, to be described. Secured centrally on one planar side (facing), in the central portion 164, is a fabricated cloth fastening means 166 (of double loops). It describes a symmetrical closed loop configuration in its relaxed state, and is bonded to the underlying padded cloth 162 at its upper and lower margins along one central transverse length. To the right side of loop 166 is an adjacent pair of complemental securing segments, which serve as in the aforedescribed restraint vest and safety harness. In one embodiment, inner pad 168 can be the adhering Velcro pad type, while outer pad 170 is then of the complemental multiple hook type. The square-cut, opposing longitudinal end 172 of device 160 is of unmodified padded, woven cloth from the center attachment line 164 of means 166.

On the opposing surface of restraint device 160, shown in FIG. 9, it has been modified to include a substantially identical, adjacent pair of complemental securing segments, 174 and 176, located transversely of the padded cloth and proximal to the left hand, longitudinal end segment. Consistent with the nature of the other pad set (168/170), inner pad 174 is of the adhesive pad type, since outer pad 170 of FIG. 8 is of the multiple hook type, so they will adhere firmly upon making contact. Likewise, since outer pad 176 (FIG. 9) is also of the multiple hook type, then inner pad 168 (FIG. 8) is of the adhesive pad type, for manifest closure reasons.

Thusly, the complemental segments of each end segment pair are arrayed so that when one restraint longitudinal end 172 is folded about a limb, and then overlaps the other squared end 178 then the adjacent segments of the one pair will make secure, but interruptable, contact with the segments of the other pair in use.

So, once a wrist is cradled within the overlappable and adhering end pads of wrist restraint 160, then the adjacent cradle padded ends 179A/179B of FIG. 8 are enfolded around the cradled wrist, are drawn in, and then engaged with a strap 100 (FIG. 4), as depicted in FIG. 10.

The thusly cuffed wrist 184 is linked to an anchoring strap 178, which has its one inner segment length 180 slipped under and around both of flexible loops 179A and 179B, and its doubled-back segment 182 running back to the buckle end (not seen) of the anchor strap 178. Anchor strap 178 is secured at the other closed end (not seen), just as are the discrete anchoring straps 100 that are employed with the restraint vest and safety belt of this invention. The dual sets of Velcro-type end pads will provide more stability to the wrist cuff and associated anchoring strap. Optionally, an adjacent, adhering pair can be on the one surface and an adjacent hooking pair on the other opposing surface.

To employ the wrist-cuffing, first wrap the patient's wrist 184 in the flexible, cloth segment 162, insuring physical comfort and safety.

Confirm that the complemental Velcro pads (168/176 and 170/174) make contact on the underneath side of the wrist. Next enfold the central loops about the limb-engaged padded restraint. Then take the snap-hook end 108 of strap 100 (FIG. 4), and pass it through both loops 179A/B on the fastening means 166. Reattach the anchor strap free end 109 to the bed frame, as earlier described. Preadjusting of the anchoring strap length may be in order to confirm proper strap tension or leeway for wrist motion.

The present invention has been described with reference to a presently preferred embodiment thereof. Such embodiment should not considered a limitation of the scope of the present invention. The scope of the present invention is better ascertained by reference to the following claims.

I claim:

1. A restraint device adapted for interruptable contact with a restrained limb and for concurrent anchoring to limit exaggerated limb flexing, comprising:
   (a) a flexible fabric member having integral padding substantially throughout and being of a generally rectangular configuration;
   (b) a flexible cloth ribbon-like means presenting a closed circle and being fastened diametrically to the opposing upper and lower margins of said fabric member along one central transverse dimension thereof, such ribbon-like means thus forming two symmetrical hemispherical loops adapted for double looping engagement with a linear strap;
   (c) a first pair of complemental pile and hook-locking segments mounted adjacently and transversely on one surface of said fabric member and being proximal to one longitudinal end of said fabric member;
   (d) a second pair of complemental pile and hook-locking segments mounted adjacently and transversely on the opposing surface of said fabric member and being proximal to the other longitudinal end of said fabric member;
   (e) the complemental segments of both pairs being arrayed so that when the one longitudinal end of the padded member is folded about a limb-like member, and acts to overlaps the other long end, that the pile segment of the first pair, will make secure contact with the hook-locking pad segment of the second pair, while the hook-locking segment of the first pair will make secure contact with the pile segment of the second pair, and
   (f) a separable anchoring strap adapted to cooperate with the two hemispherical loops of said ribbon-like means along the intermediate length of said anchoring strap by passing through said loops while they are disposed in their limb restraining mode, with the opposing ends of said anchoring strap itself terminating in mateable elements which form an anchor strap joinder and release means, and being of an intermediate length sufficient for such engaged strap to also be looped around a support post which is spaced apart from the wrist restraint device, whereby the overall flexing play of the restrained limb is controlled by the associated anchoring strap running through the double loops of the ribbon-like cloth means.

2. The restraint device of claim 1 in which the mateable elements of the anchoring strap comprises a ring-like closure means secured at one free end and a manually-activated hooking means disposed at the other strap free end.

3. The restraint device of claim 1 in which the complemental adhering segments of both pairs are rearranged so that when the one fabric member longitudinal end is folded about to overlap the other long end of the fabric member, that an first pair of adjacent pile segments will then make secure contact with the opposing second pair of adjacent hook-locking segments that are disposed oppositely at the other longitudinal end.

* * * * *